United States Patent

Crast, Jr. et al.

[11] 4,125,716
[45] Nov. 14, 1978

[54] METHOXYMETHYL ESTERS OF SUBSTITUTED IMIDAZOLIDINYL-3-METHYL-3-CEPHEM-4-CARBOXYLIC ACIDS

[75] Inventors: Leonard B. Crast, Jr., North Syracuse; Robert G. Graham, Syracuse, both of N.Y.

[73] Assignee: Bristol-Myers Company, New York, N.Y.

[21] Appl. No.: 861,334

[22] Filed: Dec. 16, 1977

[51] Int. Cl.² .............................................. C07D 501/20
[52] U.S. Cl. ...................................... 544/28; 424/246
[58] Field of Search ................................. 544/30, 28

[56] References Cited

U.S. PATENT DOCUMENTS

| Re. 29,164 | 3/1977 | Crast | 260/243 C |
|---|---|---|---|
| 3,489,752 | 1/1970 | Crast | 260/243 C |
| 3,714,146 | 1/1973 | Gottstein et al. | 260/243 C |
| 3,862,004 | 1/1975 | Takahashi et al. | 260/243 C |
| 3,996,236 | 12/1976 | Sleezer | 260/306.7 |

Primary Examiner—Nicholas S. Rizzo
Attorney, Agent, or Firm—Richard R. Lloyd

[57] ABSTRACT

Compounds of the formula

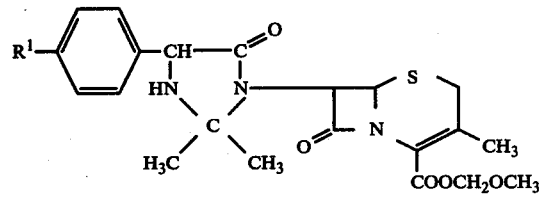

in which $R^1$ is hydrogen or hydroxy are potent antibacterial agents.

3 Claims, No Drawings

METHOXYMETHYL ESTERS OF SUBSTITUTED IMIDAZOLIDINYL-3-METHYL-3-CEPHEM-4-CARBOXYLIC ACIDS

BACKGROUND OF THE INVENTION

1. Field of the Invention

This invention relates to the methoxymethyl esters of certain substituted imidazolidinyl-3-methyl-3-cephem-4-carboxylic acids.

2. Description of the Prior Art

A. U.S. Pat. No. 3,714,146 discloses and claims, inter alia, 7-(D-2,2-dimethyl-5-oxo-4-phenyl-1-imidazolidinyl)-3-methyl-3-cephem-4-carboxylic acid [hereinafter referred to as hetacephalexin], having the formula

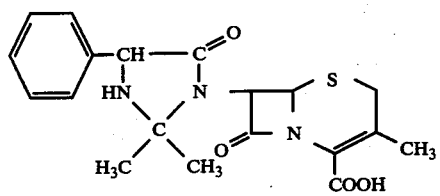

B. U.S. Pat. No. 3,489,752 and its reissue U.S. Pat. No. Re29,164 disclose and claim, inter alia, 7-[D-2,2-dimethyl-4-(p-hydroxyphenyl)-5-oxo-1-imidazolidinyl]-3-methyl-3-cephem-4-carboxylic acid [hereinafter referred to as hetacefadroxil], having the formula

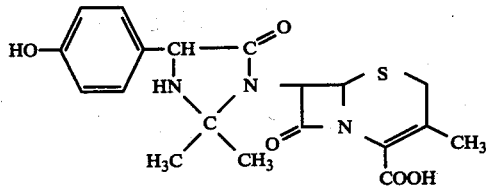

The specification contains the very general statement "Also included are the easily hydrolyzed esters or amides of such acids which may be converted to the free acid form by chemical or enzymatic hydrolysis", but no such ester are exemplified or named.

C. U.S. Pat. No. 3,862,004 discloses and claims a process for the preparation of cephalosporins of the formula

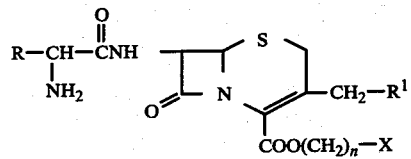

in which, inter alia, R may be phenyl or p-hydroxyphenyl, $R^1$ may be hydrogen, $n$ may be 1 and X may be methoxy. The process comprises enzymatic coupling of the appropriately substituted 7-amino-3-cephem compound with an acid of the formula $R-CH(NH_2)COOH$.

When $R^1$ is hydrogen, $n$ is 1, $R^1$ is methoxy and R is either phenyl or p-hydroxyphenyl, the compound is the methoxymethyl ester of cephalexin or the methoxymethyl ester of cefadroxil, respectively.

D. U.S. Pat. No. 3,996,236 discloses and claims the methoxymethyl ester of hetacillin, having the formula

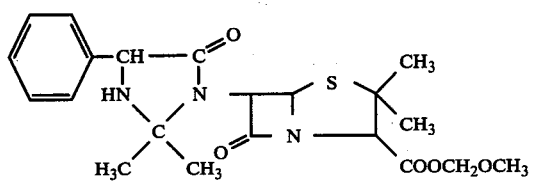

E. French Published Patent Application No. 2,319,353 discloses and claims the methoxymethyl ester of the acetone adduct of amoxycillin, having the formula

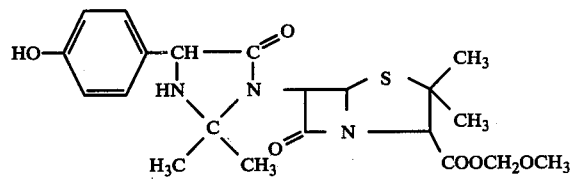

F. The prior art contains numerous patents and publications directed to the preparation of deacetoxy cephalosporins (3-methyl-$\Delta^3$-cephems) by ring enlargement reactions of penicillin sulfoxides. Some of this art make general statements to the effect that substantially any known penicillin side chain is suitable for use in the reaction. Alternatively, the art teaches that the resulting 3-methyl-$\Delta^3$-cephem compound may be cleaved to produce 7-ADCA and then re-acylated with substantially any side chain. During the ring enlargement reaction the carboxyl group of the penicillin sulfoxide must be protected to prevent decarboxylation. This is often done by utilizing as ester of the penicillin sulfoxide—the product being the corresponding 3-methyl-$\Delta^3$-cephem ester. Despite the voluminous prior art generated by numerous workers in this field, the instantly claimed compounds have not, to our knowledge, been described or disclosed in any of such prior art. The following patent is cited as representative of broad disclosure patents in the ring enlargement field.

U.S. Pat. No. 3,944,545 discloses a process for preparing substituted 3-methyl-3-cephem compounds via ring expansion of the corresponding penicillin sulfoxide. In its broad disclosure of suitable side chains of the formula

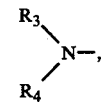

$R_3$ and $R_4$ are defined as "an amino protecting group". Several broad sub-generic classes of side chains are given, including one in which $R_3$ and $R_4$, taken together with the nitrogen atom to which they are attached, may be "phthalimido, a cyclic imide moiety of a $C_3$-$C_{12}$ dicarboxylic acid, 2,2-dimethyl-5-oxo-4-phenylimidazolidin-1-yl, 2,2-dimethyl-3-nitroso-5-oxo-4-phenylimidazolidin-1-yl, or the like". As to the carboxyl group, the patent discloses the group —$COOR_2$ in which $R_2$ "is a carboxy protecting group". A broad list of preferred carboxy protecting groups is given, but methoxymethyl is not encompassed thereby. The patent specifically discloses the preparation of the p-nitrobenzyl ester of 7-(2,2-dimethyl-5-oxo-4-phenylimidazolidin-1-yl)-3-methyl-3-cephem-4-carboxylic acid.

SUMMARY OF THE INVENTION

Compounds of the formula

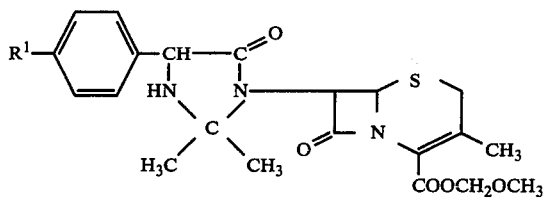

wherein $R^1$ is hydrogen or hydroxy are potent antibacterial agents which are lipid-soluble and give significantly higher tissue levels following oral administration than their parent compounds cephalexin and cefadroxil.

COMPLETE DISCLOSURE

Cephalexin and cefadroxil are known cephalosporins having the Formula II

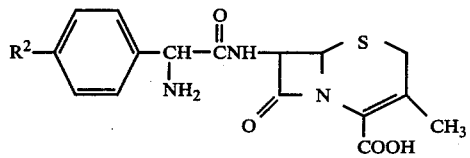

in which $R^2$ is hydrogen and hydroxy, respectively. In common with other cephalosporins and penicillins, cephalexin and cefadroxil are ionized, water-soluble compounds at the pH of blood plasma, which greatly limits their ability to traverse cell membranes and achieve high tissue levels, except in the organs of excretion (liver and kidney).

In the treatment of bacterial infection, the concentration of antibacterial agent in infected tissue is as important as serum levels. It therefore was an object of this invention to prepare lipid-soluble derivatives of lipid-insoluble cephalexin and cefadroxil, which would produce higher tissue levels of antibiotic following oral administration than do the parent compounds. This object has been met by the provision, according to the present invention, of the methoxymethyl ester of heta-cephalexin and the methoxymethyl ester of hetacefadroxil, having the formula

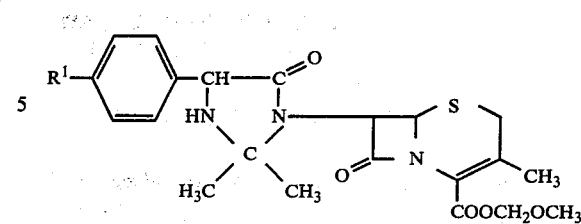

in which $R^1$ is hydrogen and hydroxy, respectively.

The compounds of Formula I may be prepared from the known compounds of Formula II by either of two routes (which are described in detail in the Examples), as follows:

(A) The compound of Formula II is reacted with acetone to form the acetone adduct of Formula III

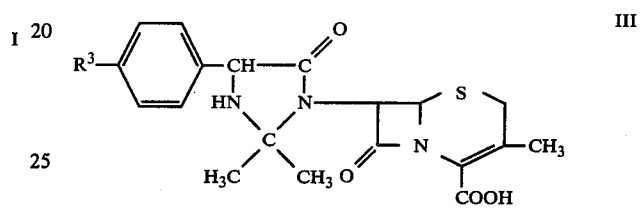

in which $R^3$ is hydrogen or hydroxy. The compound of Formula III is then converted to its methoxymethyl ester (as by reaction with bromomethyl methyl ether) to produce the compound of Formula I.

(B) The compound of Formula II is converted to its methoxymethyl ester (as by reaction with bromomethyl methyl ether) having the Formula IV

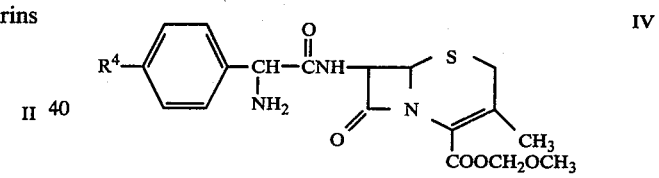

in which $R^4$ is hydrogen or hydroxy. The compound of formula IV is then converted to the compound of Formula I by reaction with acetone to form the acetone adduct.

Alternatively, the compounds of Formula I may be prepared by acylating the methoxymethyl ester of 7-ADCA with an acylating derivative of an acid of Formula V

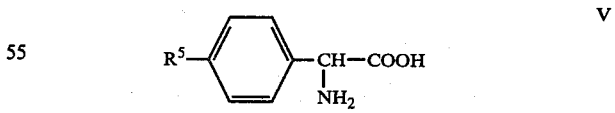

in which $R^5$ is hydrogen or hydroxy, to produce a compound of Formula IV, which is then reacted with acetone, as described above, to produce the compound of Formula I. Suitable acylating derivatives of the acid, and reaction conditions for the acylation, are set forth in U.S. Pat. No. 3,996,236, the contents of which are incorporated herein by reference.

The Minimum Inhibitory Concentrations of the compounds of Formula I and of cephalexin and cefadroxil were determined against various microorganisms by the tube dilution technique after overnight incubation in Nutrient Broth at 37° C., and the results are shown in Table 1. The methoxymethyl esters of hetacephalexin and hetacefadroxil are the compounds of Formula I wherein $R^1$ is hydrogen and hydroxy, respectively.

The plasma and tissue levels of the methoxymethyl ester of hetacephalexin and of cephalexin were determined in rats, after oral administration (lung and brain were selected as examples of therapeutically significant organs).

Table 1

| Organism | | Minimum Inhibitory Concentration (mcg./ml.) | | | |
|---|---|---|---|---|---|
| | | Methoxymethyl Ester Of | | | |
| | | Hetacephalexin | Hetacefadroxil | Cephalexin | Cefadroxil |
| Streptococus pneumoniae | A9585 | 1 | 1 | 1 | 1 |
| Streptococcus pyogenes | A9604 | 0.25 | 0.25 | 0.5 | 0.25 |
| Staphylococcus aureus | A9537 | 1 | 1 | 1 | 1 |
| Staph aureus + 50% serum | A9537 | 2 | 2 | 2 | 2 |
| Escherichia coli | A15119 | 8 | 32 | 8 | 16 |
| Klebsiella pneumoniae | A15130 | 16 | 63 | 16 | 32 |
| Proteus mirabilis | A9900 | 8 | 8 | 4 | 8 |
| Proteus morganii | A15153 | 125 | 125 | >125 | >125 |
| Serratia marcescens | A20019 | >125 | >125 | >125 | >125 |
| Enterobacter cloacae | A9659 | 125 | >125 | >125 | >125 |
| Enterobacter cloacae | A9656 | 125 | 125 | >125 | >125 |
| Pseudomonas aeruginosa | A9843A | >125 | >125 | >125 | >125 |

Thirty-six healthy male Sprague-Dawley rats (Charles River Laboratories) weighing 200–250 g were randomly divided into two treatment groups of 16 rats each and one group of 4 control rats. Following a 24 hour fast (water ad. lib.), one group of 16 rats was administered, by oral intubation, a 200 mg/kg dose of cephalexin monohydrate and the other group a dose of the methoxymethyl ester of hetacephalexin equivalent to 200 mg/kg of cephalexin monohydrate. Each compound was dissolved in glycerol formal (Lot No. E27103, Center Chemical Co., Inc., N.Y.C. N.Y.) at a concentration equal to 40 mg of cephalexin monohydrate per ml. An equal volume of deionized water was added to yield a final concentration of 20 mg of cephalexin monohydrate equivalent per ml. The dosing solutions were stored in an ice bath, used within 6 hours of preparation and an aliquot of each solution was retained for assay.

Rats in each treatment group were administered 1 ml of dosing solution per 100 g of body weight. The four additional control rats were administered a glycerol formal:deionized water (1:1) solution (1ml/100 g b.w.) to serve as a vehicle control group. The group receiving the methoxymethol ester of hetacephalexin and the vehicle control group were run on one day and the cephalexin group on the following day.

Four rats from each treatment group and one rat from the vehicle control group were killed 15, 30, 60 and 120 minutes after dosing. The rats were killed by exsanguination at the bifurcation of the femoral arteries while they were under light ether anesthesia. Approximately 10 ml of blood were obtained from each rat in 10 ml disposable syringes which had been previously rinsed with a 1% Na heparin in 0.9% NaCl solution. Each sample was immediately transferred from the syringe, after removing the needle, to a heparinized vacutainer tube, gently inverted a few times to mix the anticoagulant and centrifuged at 3000 rpm for 5 minutes in a refrigerated centrifuge at 4° C. to separate plasma. Plasma was transferred to a polypropylene snap-cap tube and stored at −20° C. until assayed. Lungs and brains were removed immediately after exsanguination, rinsed with ice-cold 0.9% NaCl solution, blotted dry with gauze, wrapped separately in pieces of aluminum foil, placed in dry ice for quick freezing and stored at −20° C. until assayed.

Concentrations of antibiotic activity in plasma and tissue samples were assayed in terms of cephalexin by a microbiologic cup-plate assay employing cephalexin monohydrate as the reference standard and *Sarcina lutea* derived from ATCC No. 9341 as the assay organism. Plasma samples were diluted with an equal volume of acetone and further diluted with a 1:1 mixture of acetone:1% pH6 phosphate buffer to a concentration approximating the midpoint of the standard curve. Tissues were homogenized with 2 volumes of 1% pH 6 phosphate buffer in a glass homogenizer with a motor driven teflon pestle. Equal volumes of homogenate and acetone were mixed and, following centrifugation, the supernatant was diluted for assay in a manner similar to plasma. Dosing solutions were diluted with acetone:1% pH 6 phosphate buffer (1:1) and assayed similar to plasma. The methoxymethyl ester of hetacephalexin dosing solution was also assayed for intact ester by diluting with pH 7.4 phosphate buffer, extracting with $CHCl_3$ (cephalexin does not partition into $CHCl_3$) and assaying the $CHCl_3$ phase for antibiotic activity.

Statistical hypotheses regarding differences in plasma and tissue level parameters were tested at the $p = 0.05$ level of significance by a "t-test" for non-paired comparisons which is integral to the Monroe 1930 Electronic Display Calculator for Statistics.

The plasma levels of cephalexin antibiotic activity following the oral administration of equimolar doses (200 mg/kg in terms of cephalexin monohydrate) of the methoxymethyl ester of hetacephalexin or cephalexin monohydrate to normal rats are shown in Table 2. The corresponding brain levels and brain to plasma concentration ratios are shown in Tables 3 and 4, respectively. The corresponding lung levels and lung to plasma concentration ratios are shown in Tables 5 and 6, respectively. The results of the assays on the retained dosing solutions are shown in Table 7. No antibiotic activity was detected in either the plasma or brain or lung tissue of the vehicle control group of rats.

Table 2

Plasma Levels of Cephalexin Antibiotic Activity Following the Oral Administration of the Methoxymethyl Ester of Hetacephalexin and Cephalexin to Rats

| Compound Administered[a] | | Plasma Level[b] (mcg/ml) | | | |
|---|---|---|---|---|---|
| | | 15 min. | 30 min. | 60 min. | 120 min. |
| Methoxymethyl Ester of Hetacephalexin | | 46 | 40 | 36 | 11 |
| | | 50 | 50 | 27 | 15 |
| | | 58 | 55 | 46 | 14 |
| | | 62 | 37 | 28 | 18 |
| | mean | 54.0 | 45.5 | 34.2[c] | 14.5[c] |
| | S.E. | 3.6 | 4.2 | 4.4 | 1.4 |
| | | 66 | 52 | 44 | 19 |

Table 2-continued

Plasma Levels of Cephalexin Antibiotic Activity Following the Oral Administration of the Methoxymethyl Ester of Hetacephalexin and Cephalexin to Rats

| Compound Administered[a] | | Plasma Level[b] (mcg/ml) | | | |
|---|---|---|---|---|---|
| | | 15 min. | 30 min. | 60 min. | 120 min. |
| Cephalexin | | 60 | 51 | 50 | 20 |
| | | 56 | 46 | 47 | 21 |
| | | 48 | 59 | 54 | 29 |
| | mean | 57.5 | 52.0 | 48.8 | 22.2 |
| | S.E. | 3.8 | 2.7 | 2.1 | 2.3 |

[a]200 mg/kg of body weight, in terms of cephalexin monohydrate.
[b]Total antibiotic activity in terms of cephalexin.
[c]Value different from corresponding cephalexin value ($p < 0.05$ level of significance).

Table 3

Brain Levels of Cephalexin Antibiotic Activity Following the Oral Administration of the Methoxymethyl Ester of Hetacephalexin and Cephalexin to Rats

| Compound Administered[a] | | Brain Level[b] (mcg./g) | | | |
|---|---|---|---|---|---|
| | | 15 min. | 30 min. | 60 min. | 120 min. |
| Methoxymethyl | | 2.6 | 1.7 | 1.7 | 0.5 |
| Ester of | | 3.2 | 2.7 | 1.5 | 0.5 |
| Hetacephalexin | | 4.2 | 2.4 | 2.5 | 0.4 |
| | | 2.4 | 1.8 | 1.3 | 0.6 |
| | mean | 3.1[c] | 2.2[c] | 1.8[c] | 0.5[c] |
| | S.E. | 0.4 | 0.2 | 0.3 | 0.0 |
| Cephalexin | | 0.6 | 0.6 | 0.6 | 0.2 |
| | | 0.4 | 0.5 | 0.6 | 0.3 |
| | | 0.4 | 0.6 | 0.7 | 0.3 |
| | | 0.4 | 0.5 | 0.4 | 0.3 |
| | mean | 0.45 | 0.55 | 0.58 | 0.28 |
| | S.E. | 0.05 | 0.03 | 0.06 | 0.02 |

[a]200 mg/kg of body weight, in terms of cephalexin monohydrate.
[b]Total antibiotic activity in terms of cephalexin.
[c]Value different from corresponding cephalexin value ($p < 0.05$ level of significance).

Table 4

Brain to Plasma Concentration Ratios of Cephalexin Antibiotic Activity Following the Oral Administration of the Methoxymethyl Ester of Hetacephalexin and Cephalexin to Rats

| Compound Administered[a] | | Brain to Plasma Ratio × 100[b] | | | |
|---|---|---|---|---|---|
| | | 15 min. | 30 min. | 60 min. | 120 min. |
| Methoxymethyl | | 5.6 | 4.2 | 4.7 | 4.6 |
| Ester of | | 6.4 | 5.4 | 5.6 | 3.3 |
| Hetacephalexin | | 7.2 | 4.4 | 5.4 | 2.9 |
| | | 3.9 | 4.9 | 4.6 | 3.3 |
| | mean | 5.8[c] | 4.7[c] | 5.1[c] | 3.5[c] |
| | S.E. | 0.7 | 0.3 | 0.2 | 0.4 |
| Cephalexin | | 0.9 | 1.2 | 1.4 | 1.0 |
| | | 0.7 | 1.0 | 1.2 | 1.5 |
| | | 0.7 | 1.3 | 1.5 | 1.4 |
| | | 0.8 | 0.8 | 0.7 | 1.0 |
| | mean | 0.8 | 1.1 | 1.2 | 1.2 |
| | S.E. | 0.0 | 0.1 | 0.2 | 0.1 |

[a]200 mg/kg of body weight, in terms of cephalexin monohydrate.
[b] $\frac{\text{Antibiotic concentration in brain}}{\text{Antibiotic concentration in plasma}} \times 100$
[c]Value different from corresponding cephalexin value ($p < 0.05$ level of significance).

Table 5

Lung Levels of Cephalexin Antibiotic Activity Following the Oral Administration of the Methoxymethyl Ester of Hetacephalexin and Cephalexin to Rats

| Compound Administered[a] | | Lung Level[b] (mcg/g) | | | |
|---|---|---|---|---|---|
| | | 15 min. | 30 min. | 60 min. | 120 min. |
| Methoxymethyl | | 43 | 23 | 22 | 4.1 |
| Ester of | | 44 | 32 | 23 | 5.2 |
| Hetacephalexin | | 47 | 28 | 25 | 4.3 |
| | | 42 | 25 | 19 | 5.3 |
| | mean | 44.0[c] | 27.0[c] | 22.3[c] | 4.7 |
| | S.E. | 1.1 | 2.0 | 1.2 | 0.3 |
| | | 19.0 | 10.0 | 17.0 | 5.6 |
| | | 9.1 | 5.9 | 7.6 | 5.4 |
| | | 7.0 | 7.2 | 12.0 | 5.3 |

Table 5-continued

Lung Levels of Cephalexin Antibiotic Activity Following the Oral Administration of the Methoxymethyl Ester of Hetacephalexin and Cephalexin to Rats

| Compound Administered[a] | | Lung Level[b] (mcg/g) | | | |
|---|---|---|---|---|---|
| | | 15 min. | 30 min. | 60 min. | 120 min. |
| | | 9.6 | 7.4 | 9.7 | 7.6 |
| | mean | 11.2 | 7.6 | 11.6 | 6.0 |
| | S.E. | 2.7 | 0.8 | 2.0 | 0.5 |

[a]200 mg/kg of body weight, in terms of cephalexin monohydrate.
[b]Total antibiotic activity in terms of cephalexin.
[c]Value different from corresponding cephalexin value ($p < 0.05$ level of significance).

Table 6

Lung to Plasma Concentration Ratios of Cephalexin Antibiotic Activity Following the Oral Administration of the Methoxymethyl Ester of Hetacephalexin and Cephalexin to Rats

| Compound Administered[a] | | Lung to Plasma Ratio × 100[b] | | | |
|---|---|---|---|---|---|
| | | 15 min. | 30 min. | 60 min. | 120 min. |
| Methoxymethyl | | 93.5 | 57.5 | 61.1 | 37.3 |
| Ester of | | 88.0 | 64.0 | 85.2 | 34.7 |
| Hetacephalexin | | 81.0 | 50.9 | 54.4 | 30.7 |
| | | 67.7 | 67.6 | 67.9 | 29.4 |
| | mean | 82.6[c] | 60.0[c] | 67.2[c] | 33.0[c] |
| | S.E. | 5.6 | 3.7 | 6.6 | 1.8 |
| Cephalexin | | 28.8 | 19.2 | 38.6 | 29.5 |
| | | 15.2 | 11.6 | 15.2 | 27.0 |
| | | 12.5 | 15.7 | 25.5 | 25.2 |
| | | 20.0 | 12.5 | 18.0 | 26.2 |
| | mean | 19.1 | 14.8 | 24.3 | 27.0 |
| | S.E. | 3.6 | 1.7 | 5.2 | 0.9 |

[a]200 mg/kg of body weight, in terms of cephalexin monohydrate.
[b] $\frac{\text{Antibiotic concentration in lung}}{\text{Antibiotic concentration in plasma}} \times 100$
[c]Value different from corresponding cephalexin value ($p < 0.05$ level of significance).

Table 7

Antibiotic Concentrations of Dosing Solutions Retained for Assay

| Solution[a] | Antibiotic Concentration[b] | Intact Ester Concentration[c] |
|---|---|---|
| Methoxymethyl Ester of Hetacephalexin | 19 mcg/ml | 19 mcg/ml |
| Cephalexin Monohydrate | 21 mcg/ml | — |
| Glycerol Formal: Deionized Water (1:1) | <0.2 mcg/ml[d] | — |

[a]Compounds were dissolved in glycerol formal followed by the addition of an equal volume of deionized water to produce a final nominal concentration equivalent to 20 mg of cephalexin monohydrate per ml.
[b]In terms of cephalexin.
[c]Assay of CHCl₃ extract which extracts only the methoxymethyl ester of hetacephalexin.
[d]The sensitivity of the cup-plate assay is 0.2 mcg/ml.

Tables 3 and 5 show that significantly higher brain and lung levels, respectively, of antibiotic activity are obtained following oral administration of the methoxymethyl ester of hetacephalexin than are obtained following the oral administration of an equivalent amount of cephalexin monohydrate. The higher brain and lung antibiotic levels obtained with the methoxymethyl ester of hetacephalexin are not the result of higher plasma levels. On the contrary, as shown in Table 2, both compounds were rapidly absorbed, achieving similar peak plasma antibiotic levels within 15 minutes of administration. Plasma levels following cephalexin administration were statistically higher throughout the 2 hour experimental period. The reason for the disproportionately higher brain and lung levels following administration of the methoxymethyl ester of hetacephalexin may best be seen by an examination of the tissue to plasma ratios of antibiotic activity.

Table 4 shows that the methoxymethyl ester of hetacephalexin peaked in the brain about 15 minutes after administration, at about 6% of its plasma level. Cephalexin, on the other hand, peaked later (60–120 minutes) at only about 1% of its plasma level. Table 6 shows that the methoxymethyl ester of hetacephalexin peaked in the lung about 15 minutes after administration, at about 83% of its plasma level. Again, cephalexin peaked later (60–120 minutes) at only 27% of its plasma level.

These qualitative and quantitative differences in the tissue to plasma ratio patterns indicate that the methoxymethyl ester of hetacephalexin more readily penetrates tissue cell membranes and crosses the blood-brain barrier than does cephalexin.

Table 7 shows that the concentrations of both dosing solutions were within 5% of their nominal concentrations of 20 mcg of cephalexin activity per ml, i.e. the assays showed 21 mcg/ml for cephalexin monohydrate and 19 mcg/ml for the methoxymethyl ester of hetacephalexin. The result of the assay performed on a $CHCl_3$ extract of the methoxymethyl ester of hetacephalexin dosing solution confirmed that the compound was administered as the intact ester since all of the antibiotic activity was $CHCl_3$ extractable.

The compounds of this invention are useful in the treatment of bacterial infections in mammals, including man. They may be administered orally or parenterally but preferably are administered orally. When used orally, the compounds of this invention may be in capsule form, or as tablets, powders, liquid solutions, suspensions, elixirs, or the like. The compounds may be used alone or in combination with other active ingredients. They may be used in compositions including one or more pharmaceutically acceptable carriers as well as other ingredients such as stabilizers, binders, antioxidants, preservatives, lubricating agents, suspending agents, viscosity controlling agents, flavors and the like. Suitable compositions are well known to those skilled in the penicillin and cephalosporin art.

The compounds of this invention may be administered over a broad dosage range, e.g. from about 5 to about 200 mg/kg of body weight per day, in divided doses. They are preferably administered over a dosage range of from about 5 to about 60 mg/kg of body weight per day, in divided doses. The most preferred adult dose is from 250 mg to 500 mg given every 6 hours.

The following examples illustrate, but do not limit, the invention.

EXAMPLE 1

Methoxymethyl Ester of Hetacephalexin

To a stirred suspension of 4.5 g (0.0116 mol) of hetacephalexin in 100 ml of dry $CH_2Cl_2$ was added 1.4 ml (0.01 mol) of triethylamine, and to the resulting solution was added 10 g of Linde 4A molecular sieves. After 30 minutes the sieves were filtered off and to the cooled and stirred filtrate (5° C.) was added 1.6 ml (0.02 mol) of bromomethyl methyl ether. After stirring 30 minutes at 5° C. the $CH_2Cl_2$ solution was washed with three 50 ml portions of cold water. The $CH_2Cl_2$ solution was then dried briefly over $Na_2SO_4$, filtered and evaporated under reduced pressure to leave an oil. The oil was triturated several times with petroleum ether (Skellysolve B) to leave a solid powder. The solids were filtered off and air dried to give 1.85 g. This material was dissolved in 25 ml of tetrahydrofuran (THF) and ether was added to the cloud point. The turbid solution was filtered and scratched. After standing 2 hours the solids were filtered off, washed with a little ether and air dried. After vacuum drying over $P_2O_5$ there was obtained 440 mg. The ir and nmr spectra were consistent for the desired structure but indicated some contaminants which were not identified. The estimated purity was 80%.

EXAMPLE 2

Methoxymethyl Ester of Hetacephalexin

A. Sodium Hetacephalexin

To a stirred slurry of cephalexin monohydrate (36.5 g; 0.1 mol) in 150 ml of acetone and 100 ml of methanol was added 43.75 ml of a 10% W/V sodium hydroxide solution in methanol over a 2 hour period, never letting the pH get above 9. The resulting solution was stirred for another hour, during which part of the product crystallized out. Acetone (750 ml) was added slowly (dropwise) over a 2 hour period. The resulting crystals were filtered off, washed with acetone and air dried. The product was further dried over $P_2O_5$ to give 33 g, dec. pt. 215° C. (sharp). The ir and nmr spectra were well defined and consistent with the desired structure.

Anal. Calc'd. for $C_{19}H_{20}N_3O_4S.Na$: C, 55.75; H, 4.93; N, 10.27; Found: C, 55.22; H, 4.90; N, 9.91; $K.F.H_2O$ = 1.16%. Found (corrected for 1.16% $H_2O$): C, 55.87; H, 4.82; N, 10.03.

B. Methoxymethyl Ester of Hetacephalexin

To a stirred slurry of 12.27 g (0.03 mole) of sodium hetacephalexin in 200 ml of dry DMAC (dimethylacetamide) at −18° C., was added, dropwise, over a 2 hour period, a solution of 2.4 ml (0.03 mol) of bromomethyl methyl ether in 60 ml of methylene chloride. One hour after the addition was complete, the near-solution, was diluted with 1 liter of ethyl acetate and extracted with six 200 ml portions of water. The organic layer was dried 10 minutes over $Na_2SO_4$ in an ice bath with stirring, the $Na_2SO_4$ was filtered off and the filtrate was concentrated in vacuo at <22° C. to an oil which was dissolved in 100 ml of acetonitrile and extracted with 3 × 50 ml of n-heptane. The acetonitrile solution was concentrated to an oil which was solidified by repeated trituration with n-heptane. The dried solid weighed 6.9 g. The solids were then slurried in 400 ml of ether for 30 minutes, filtered, and air dried to give 5.5 g. This material was slurried in 200 ml of methylcylohexane and scratching appeared to induce crystallization. After slurrying 1 hour the product was filtered off, washed with methylcyclohexane and air dried. After vacuum drying over $P_2O_5$ there was obtained 4.8 g; nmr analysis indicated the product to be 80–90% pure.

A total of 2 g of the above material was dissolved in 22 ml of THF and diluted to the cloud point with ether. After about 30 minutes the resulting precipitate was filtered off. The filtrate was warmed slightly and ether was added to the cloud point once again. After 30 minutes the resulting precipitate was filtered off and the filtrate once again was warmed, diluted to the cloud point, allowed to stand 30 minutes and filtered. This time the filtrate was evaporated in vacuo at >22° C. to an oil which was triturated with two 20 ml portions of ether. The gummy solids were then triturated with 25 ml of cyclohexane until solid. The solids were filtered off, washed with cyclohexane, ground up in a mortar while still wet and allowed to air dry. After vacuum drying over $P_2O_5$ there was obtained 1.2 g of crystalline material; the ir and nmr spectra were consistent with the desired structure and showed the product to be at least 95% pure. M.P. 107° C. with decomposition.

Anal. Calc'd. for $C_{21}H_{25}N_3O_5S$: C, 58.33; H, 5.83; N, 9.72. Found: C, 58.39; H, 5.51; N, 9.51.

EXAMPLE 3

Methoxymethyl Ester of Hetacephalexin

Example 2 was repeated except that, in Step B, the workup was simplified by taking the acetonitrile concentrate (oil) and going directly to the THF-ether fractionating procedure followed by cyclohexane trituration etc., to give 6.2 g of crystalline material, M.P. 107° C. dec. with melting. The ir and nmr spectra were comparable to the reference material Anal. Calc'd for $C_{21}H_{25}N_3O_5S$: C, 58.33; H, 5.83; N, 9.72; Found: C, 58.17, 58.59; H, 5.99, 5.86; N, 10.22, 9.65. K.F.$H_2O$ = 1.12%.

EXAMPLE 4

Methoxymethyl Ester of Hetacefadroxil

A. Sodium Hetacefadroxil

To a stirred suspension of 37.7 g (0.095 mol) of cefadroxil hydrate in 200 ml of acetone and 150 ml of methanol was added, dropwise, over a 2 hour period, a solution of 10% NaOH (43 ml) in methanol keeping the pH below 9 throughout the addition. The resulting solution soon began to deposit a gelatinous precipitate and after 1 hour 600 ml of acetone was added with vigorous stirring. After 30 minutes this slurry was poured into 1.2 liters of acetone with good stirring and after an additional 30 minutes the white precipitate was filtered off, washed with 3 × 200 ml of acetone and then 2 × 200 ml of petroleum ether (Skellysolve B). The product was air dried and then vacuum dried over $P_2O_5$ to give 40 g; dec. pt. 250°-255° C. with darkening above 200° C. The ir and nmr spectra were entirely consistent for the desired structure.

Anal. Calc'd for $C_{19}H_{20}N_3O_5S.Na$: C, 53.65; H, 4.74; N, 9.88; Found: C, 50.79; H, 5.17; N, 9.19; K.F.$H_2O$ = 6.21%. Found (corrected for 6.21% $H_2O$): C, 54.15; H, 4.90; N, 9.82.

B. Methoxymethyl Ester of Hetacefadroxil

To a stirred partial solution of 24.5 g (0.058 mol) of sodium hetacefadroxil in 300 ml of DMAC dried 24 hours over 3A molecular sieves) precooled to −14° C., was added dropwise, a solution of 4.8 ml (0.06 mol) of bromomethyl methyl ether in 60 ml of $CH_2Cl_2$, over a 45 minute period. Fifteen minutes after the addition was complete, the cooling bath was removed and the mixture was stirred for 1 hour. The final temperature was 17° C. The resulting clear solution was poured into 1 liter of ethyl acetate and this was washed with 6 × 200 ml of cold water. The ethyl acetate solution was dried for 10 minutes over $Na_2SO_4$ with stirring and cooling and then filtered. The ethyl acetate was removed in vacuo at <22° C. to leave an oil which was dissolved in 100 ml of THF and diluted to the cloud point with ether. After about 15 minutes the turbid solution was filtered and the procedure of dilution, addition of ether, then filtration was repeated four more times. Finally, 500 ml of ether was added slowly and the white precipitate which formed was filtered off. After air drying it weighed 5 g. This was stirred for 1 hour in 200 ml of n-hexane and then filtered. The yield was 4.9 g. After vacuum drying over $P_2O_5$ at <1 mm Hg pressure the yield was 4.7 g. The ir and nmr spectra were consistant for the desired structure. The M.P. was 110°-115° C. with decomposition. The estimated purity was 85-90%.

Anal. Calc'd for $C_{21}H_{25}N_3O_6S$: C, 56.25; H, 5.63; N, 9.38; Found: C, 54.54; H, 5.59; N, 9.15. K.F.$H_2O$ = 2.25%. Found (corrected for 2.25% $H_2O$: C, 55.80; H, 5.46; N, 9.36.

EXAMPLE 5

Methoxymethyl Ester of Hetacephalexin

A. Sodium Cephalexin

To 125 ml of methanol was added 19 g (0.055 mol) of cephalexin and, with stirring, a 10% W/V sodium hydroxide solution in methanol was added dropwise over a 2 hour period, keeping the pH below 9 (approx. 24 ml was added). The reaction mixture was stirred 15 minutes and then added to 1 liter of stirred ethyl acetate. Then additional ethyl acetate was added to a total volume of 3 liters. After stirring 1 hour at 22° C., the product was filtered off, washed with ethyl acetate and air dried. It was then dried over $P_2O_5$ in vacuo for 16 hours. The nmr was consistent for the desired structure.

B. Methoxymethyl Ester of Cephalexin

To 100 ml of DMAC was added 7.4 g (0.02 mol) of sodium cephalexin and the solution was cooled to −14° C. Then, with stirring, a solution of 1.6 ml (0.02 mol) of bromomethyl methyl ether in 40 ml of methylene chloride was added dropwise over a 2 hour period. After the addition was complete the mixture was stirred 1 hour at −14° C. and then diluted with 500 ml of ethyl acetate. It was washed with 5 × 100 ml $H_2O$ and the organic layer was dried over $Na_2SO_4$. The $Na_2SO_4$ was filtered off and the filtrate concentrated in vacuo at <22° C. to an oil. It was triturated with methyl cyclohexane to yield a solid weighing 3.2 g. The nmr spectra indicated the product to be approx. 80% pure.

This material was dissolved in 35 ml of THF and ether was added in portions up to the cloud point. After stirring 10 minutes the resulting precipitate was filtered off and additional ether was added to the filtrate up to the cloud point. It was stirred 10 minutes, the resulting precipitate was filtered off and additional ether added to the filtrate. After stirring 10 minutes the resulting precipitate was filtered off and a large excess of ether was added to the filtrate. It was stirred 30 minutes and the product was filtered off, washed with ether and air dried. After drying over $P_2O_5$ in vacuo there was obtained 1.55 g. The nmr was consistent for the desired structure and indicated at least 90% purity. The m.p. was 140°-145° C. with decomposition.

Anal Calc'd. for $C_{18}H_{21}N_3O_5S$: C, 55.23; H, 5.41; N, 10.73. Found: C, 55.41; H, 5.24; N, 10.32.

C. Methoxymethyl Ester of Hetacephalexin

A 5% solution of the methoxymethyl ester of cephalexin in acetone is allowed to stand for 24 hours at room temperature and the acetone is then removed in vacuo. The resulting gum is purified by the THF-ether fractionating procedure followed by cyclohexane trituration, etc. as described in Example 2B, to give purified methoxymethyl ester of hetacephalexin.

EXAMPLE 6

Methoxymethyl Ester of Hetacefadroxil

A. Sodium Cefadroxil

To 500 ml of methanol was added 38.1 g (0.1 mol) of cefadroxil and, with stirring, a 10% W/V sodium hydroxide solution in methanol was added over a 2 hour period, keeping the pH below 9. (A total of 43 ml was added.) This was stirred 1 hour and added to 3 liters of ethyl acetate. After stirring 1 hour at 22° C., the product was filtered off, washed with ethyl acetate and dried over $P_2O_5$ in vacuo. There was obtained 27 g. The nmr was consistent for the desired structure.

B. Methoxymethyl Ester of Cefadroxil

To 100 ml of DMAC was added 7.7 g (0.02 mol) of sodium cefadroxil and the mixture was cooled to $-17°$ C. Then, with stirring, a solution of 1.6 ml (0.02 mol) of bromomethyl methyl ether (Aldrich) in 40 ml methylene chloride was added dropwise over a 2 hour period. After the addition was complete the reaction mixture was stirred at $-14°$ C. for 1 hour. It was then diluted with 500 ml of ethyl acetate and extracted with 5 × 100 ml $H_2O$. The organic layer was dried over $Na_2SO_4$, filtered, and the filtrate concentrated in vacuo to an oil. This oil was dissolved in 25 ml THF and ether was added to the cloud point. After stirring 10 minutes the resulting precipitate was filtered off and additional ether added. This was stirred 10 minutes and the resulting precipitate filtered off. Then excess ether was added to the filtrate and the product precipitated out. It was stirred 1 hour and filtered off, washed with ether and air dried. it was then dried over $P_2O_5$ in vacuo to yield 1.2 g. The nmr was consistent for the desired structure and indicated the product to be at least 90% pure. The m.p. was 205°–210° C. with decomposition.

Anal. Calc'd for $C_{18}H_{21}N_3O_6S$: C, 53.06; H, 5.20; N, 10.31. Found: C, 52.84; H, 5.06; N, 9.75.

C. Methoxymethyl Ester of Hetacefadroxil

A 5% solution of the methoxymethyl ester of cefadroxil in acetone is allowed to stand for 24 hours at room temperature and the acetone is then removed in vacuo. The resulting gum is purified by the THF-ether fractionating procedure followed by stirring in n-hexane, etc. as described in Example 4B, to give purified methoxymethyl ester of hetacefadroxil.

We claim:

1. The D form of a compound of the formula

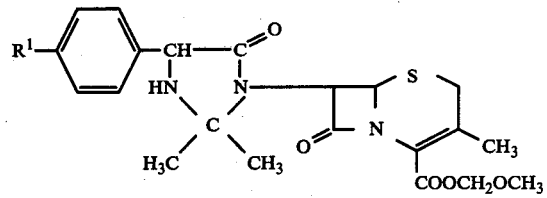

in which $R^1$ is hydrogen or hydroxy.

2. The D form of the compound of the formula

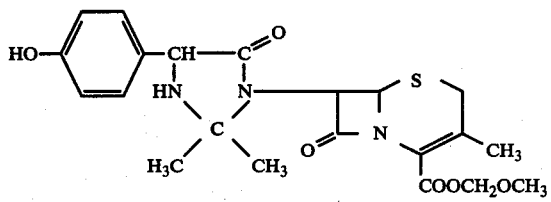

3. The D form of the compound of the formula

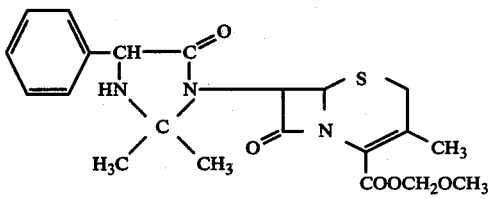

* * * * *